(12) United States Patent
Dubey

(10) Patent No.: US 11,160,641 B2
(45) Date of Patent: Nov. 2, 2021

(54) ONE STEP GINGIVA RETRACTION AND IMPRESSION MATERIAL AND METHOD

(71) Applicant: Centrix, Inc., Shelton, CT (US)

(72) Inventor: Ryan Dubey, Meriden, CT (US)

(73) Assignee: Centrix, Inc., Shelton, CT (US)

( * ) Notice: Subject to any disclaimer, the term of this patent is extended or adjusted under 35 U.S.C. 154(b) by 309 days.

(21) Appl. No.: 15/904,747

(22) Filed: Feb. 26, 2018

(65) Prior Publication Data

US 2018/0177574 A1  Jun. 28, 2018

Related U.S. Application Data

(63) Continuation of application No. PCT/US2016/049790, filed on Aug. 31, 2016.

(60) Provisional application No. 62/213,749, filed on Sep. 3, 2015.

(51) Int. Cl.
*A61K 6/69* (2020.01)
*A61K 6/90* (2020.01)
*A61C 9/00* (2006.01)

(52) U.S. Cl.
CPC .......... *A61C 9/0006* (2013.01); *A61C 9/0033* (2013.01); *A61K 6/69* (2020.01); *A61K 6/90* (2020.01)

(58) Field of Classification Search
CPC ....... A61C 9/0006; A61C 9/00; A61C 9/0033; A61K 6/90; A61K 6/69
See application file for complete search history.

(56) References Cited

U.S. PATENT DOCUMENTS

| | | | |
|---|---|---|---|
| 5,676,543 A | 10/1997 | Dragan | 433/136 |
| 6,890,177 B2 | 5/2005 | Dragan | 433/136 |
| 7,189,075 B2 | 3/2007 | Dragan | 433/136 |
| 7,195,483 B2 | 3/2007 | Dragan | 433/136 |
| 7,241,143 B2 | 7/2007 | Discko, Jr. et al. | 433/136 |
| 7,549,862 B2 | 6/2009 | Kollefrath et al. | 433/136 |

(Continued)

FOREIGN PATENT DOCUMENTS

| | | |
|---|---|---|
| JP | 2609488 B2 | 5/1997 |
| WO | WO 93/17654 | 9/1993 |

(Continued)

OTHER PUBLICATIONS

Notification of transmittal of the International Search Report and the Written Opinion of the International Searching Authority dated Feb. 3, 2017 in corresponding PCT application No. PCT/US2016/49790, 11 pages.

*Primary Examiner* — Heidi M Eide
*Assistant Examiner* — Drew S Folgmann
(74) *Attorney, Agent, or Firm* — Fattibene and Fattibene LLC; Paul A. Fattibene

(57) ABSTRACT

A dental retraction and impression system providing self-retracting and impression taking of a prepared tooth in one step. Paired setting materials simultaneously retract gingiva, widen a sulcus around the tooth, and take an impression of the tooth and margins. A low viscosity setting gingival retracting impression material having an astringent and a high viscosity setting impression material set together. The high viscosity setting impression material is heavy body and has a higher viscosity than the low viscosity setting gingival retracting material so as to force the low viscosity setting gingival retracting impression material into the gingival space or sulcus.

11 Claims, 2 Drawing Sheets

(56) References Cited

U.S. PATENT DOCUMENTS

| | | |
|---|---|---|
| 7,942,669 B2 | 5/2011 | Dragan et al. ................ 433/136 |
| 8,470,905 B2 | 6/2013 | Dragan et al. ................ 523/105 |
| 2006/0247327 A1* | 11/2006 | Klettke ................... A61K 6/90 |
| | | 523/109 |
| 2007/0160952 A1* | 7/2007 | Kollefrath ............ A61C 9/0033 |
| | | 433/136 |
| 2009/0061379 A1 | 3/2009 | Yamamoto et al. ............ 433/24 |
| 2010/0255443 A1 | 10/2010 | Dragan ......................... 433/136 |
| 2012/0329006 A1 | 12/2012 | Pierson et al. .................. 433/90 |
| 2013/0260330 A1* | 10/2013 | Marumori ............ A61C 9/0006 |
| | | 433/36 |

FOREIGN PATENT DOCUMENTS

| WO | WO 2007/117411 | 10/2007 |
|---|---|---|
| WO | WO 2019/036224 | 2/2019 |

\* cited by examiner

ONE STEP GINGIVA RETRACTION AND IMPRESSION MATERIAL AND METHOD

RELATED APPLICATIONS

This application is a continuation of International Application PCT/US2016/49790, with an international filing date of Aug. 31, 2016, which claims the benefit of U.S. Provisional Application Nos. 62/213,749 filed Sep. 3, 2015, all of which are herein incorporated by reference.

FIELD OF THE INVENTION

The present invention relates in general to retraction of gingiva around a prepared tooth, and particularly to a method and material capable of providing both retraction of gingiva and forming an impression in a single step.

BACKGROUND OF THE INVENTION

In restoring a tooth it is often necessary to retract gingiva from around the tooth in preparation for taking an impression of the tooth and surrounding gingiva. The impression is used in the making of a crown, bridge, inlay, or overlay to fit over the prepared tooth. It is essential that a good impression of the area around the prepared tooth be taken so that the crown, crown, bridge, inlay, or overlay fits properly on the prepared tooth.

The retraction of the gingiva from around the prepared tooth is often labor-intensive and difficult. There have been many efforts to provide an easier more convenient way to retract gingiva so that an accurate impression can be made. One such device and method is disclosed in U.S. Pat. No. 7,942,669 entitled "Gingiva Tissue Retraction Device and Method" issuing on May 17, 2011 to Dragan et al., which is herein incorporated by reference. Therein disclosed is a pre-dosed prepared cap used in gingival retraction having an initially inactive dry astringent.

Another device and method is disclosed in U.S. Pat. No. 7,189,075 entitled "Method and Device for the Retraction and Hemostasis of Tissue During Crown and Bridge Procedures" issuing on Mar. 13, 2007 to Dragan et al., which is herein incorporated by reference. Therein disclosed is a method of retracting gum tissue by placing an initially flowable material around a tooth, covering the tooth and initially flowable material with a dam mad of a porous material, applying pressure until the initially flowable material sets, and removing the dam with the initially flowable material attached.

While these prior methods and materials made the taking of impressions easier they involve multiple steps and have been time consuming to perform. Therefore, there is a need for a method and material that can simultaneously retract gingiva and take an impression in a single operation making dentistry easier.

SUMMARY OF THE INVENTION

The present invention makes it easier to take an impression of a prepared tooth by combining the retraction and impression in a single operation. A first low viscosity setting gingival retracting impression material is applied with a syringe around the interface of the gingiva and the tooth. Soon thereafter and before the first low viscosity setting gingival retracting impression material has set a second high viscosity setting impression material is applied over the first low viscosity setting gingival retracting impression material. The setting times of the first and second material are synchronized so they set together. The setting of the two materials may be controlled by a chemical reaction, such as use of a catalyst. The first and second material are then removed together forming an impression of the gingiva and prepared tooth. The first low viscosity setting gingival retracting impression material preferably contains a retracting agent, such as an astringent.

It is an object of the present invention to make the taking of a dental impression easier and quicker.

It is an advantage of the present invention that retraction of gingiva and the taking of an impression are accomplished in a single operation.

It is another advantage of the present invention that a low viscosity setting gingival retracting impression material and the high viscosity setting impression material are set and removed at the same time.

It is a feature of the present invention that the first low viscosity setting gingival retracting impression material and the high viscosity setting impression material have setting times that are synchronized so that they both set at approximately the same time.

It is another feature of the present invention that the first low viscosity setting gingival retracting impression material contains a retracting agent, an astringent, or hemostatic agent.

It is yet another feature of the present invention that the second high viscosity setting impression material has a viscosity higher than the first low viscosity setting gingival retracting impression material.

It is yet another feature of the present invention that the second high viscosity setting impression material is heavy body and has a mousse-like consistency.

These and other objects, advantages, and features will become more readily apparent in view of the following more detailed description.

DETAILED DESCRIPTION OF THE INVENTION

Figure 1:
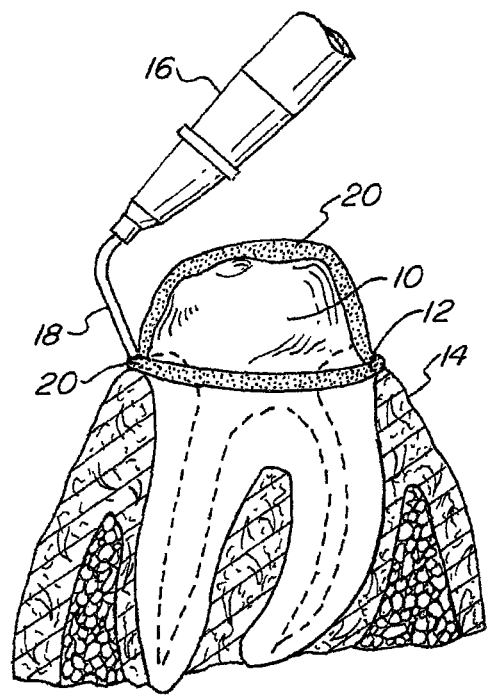
FIG. 1 schematically illustrates the present invention and application of a low viscosity setting gingival retracting impression material.
Figure 2:
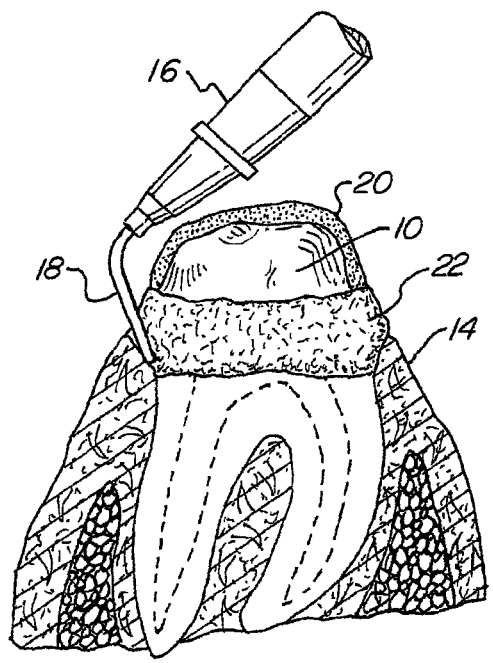
FIG. 2 schematically illustrates the present invention and application of a high viscosity setting impression material.

FIGS. 1 and 2 illustrate the present invention. In FIG. 1 a prepared tooth 10 is surrounded by gingiva 14. A space or sulcus is formed between or at the margin of the gingiva 14 and the surface of the paired tooth 10. A syringe tip 16, attached to a syringe, not illustrated, has a cannula 18 thereon. The cannula 18 may be made of a malleable metal to facilitate placement and positioning. The cannula 18 may have a relatively small gauge to facilitate accurate placement of a low viscosity setting gingival retraction impression material 20 around the perimeter, and preferably around the entire exposed surface of the prepared tooth 10. The syringe tip 16 preferably has a mixing portion that has an augur for mixing two component materials. The low viscosity setting gingival retraction impression material 20 is extruded by the syringe through the syringe tip 16 and the cannula 18. The material 20 has a relatively low viscosity and contains a retracting agent, such as an astringent or hemostatic agent such as aluminum chloride, aluminum potassium sulfate, aluminum sulfate, alum, ferric sulfate or any other known retracting agent.

FIG. 2 illustrates the placement of a high viscosity setting impression material 22 around the perimeter of the prepared tooth 10 on top of the low viscosity setting gingival retraction impression material 20, illustrated in FIG. 1. The high viscosity setting impression material 22 may be placed on top of the low viscosity setting gingival retraction impression material 20 with a syringe, or preferably with a dental tray filled with the high viscosity setting impression material 22. The material 22 has a higher viscosity than the material 20. Additionally material 22 may, but generally need not contain a retracting agent.

The low viscosity setting gingival retracting impression material 20 has a setting time that is synchronized with the high viscosity setting impression material 22 so that the two materials 20 and 22 will set together forming a single unitary mold. Upon removal of the single unitary mold the impression of the prepared tooth 10 and the gingiva 14, including the sulcus 12 is formed. This impression may then be used as a mold in preparing a crown, bridge, inlay or overly to cover the prepared tooth.

The low viscosity setting gingival retracting impression material 20 preferably has a viscosity so that it can easily flow into the sulcus 12 around the prepared tooth 10 so as to form an accurate impression. The low viscosity setting gingival retracting impression material 20 also contains a retracting agent so that the gingiva 14 is retracted from the surface of the prepared tooth 10 so as to make possible the taking of a more detailed impression of the prepared tooth 10 so as to provide a good quality impression. The high viscosity setting impression material 22 has a higher viscosity than the low viscosity setting gingival retracting impression material so as to provide a heavier backing material to gently force the low viscosity setting gingival retracting impression material 20 into the sulcus 12. The higher viscosity setting impression material 22 is heavy body and has a mousse-like consistency. The higher viscosity setting impression material 22 has a stiffness sufficient to force or drive the low viscosity setting gingival retracting impression material into the sulcus 12 around the prepared tooth 10. The high viscosity setting impression material 22 preferably has a hardness when set greater than the low viscosity setting gingival retracting impression material 20 when set. The high viscosity setting impression material 22 may have a Shore hardness type A scale greater than eighty when set. Shore hardness is measured with a durometer. This aids in retraction and providing a good impression. This also prevents injury to the gingiva by providing a compliant yet firm force. The heavier setting or high viscosity setting impression material 22 also provides additional strength when combined or attached to the low viscosity setting gingival retracting impression material 20 while also facilitating the removal of the combined single unitary mold from the prepared tooth 10 and the gingiva 14 without breaking or separating so as to provide an accurate impression. A syringe or a dental impression tray may be used to apply the high viscosity setting impression material 22 to the prepared tooth 10 and the low viscosity setting gingival retracting impression material 20.

Both impression materials 20 and 22 are preferably based on a vinylpolysiloxane or VPS impression material. The VPS impression material has a combination of physical properties that provide strength, elasticity, dimensional stability, and the ability to register detail in any environment. The VPS impression material can provide a wide selection of viscosities and set times. The VPS material has two components that when mixed set into a flexible solid.

Preferably, the low viscosity setting gingival retracting impression material is thinned to a consistency of a wash type material having a viscosity of 120,000 to 150,000 cP or centipoise at room temperature. For example, water has a viscosity of 0.899 cP at 25° C. This low viscosity setting gingival retracting impression material 20 is placed by the tip 16 and syringe, not shown, around the sulcus and over the tooth to provide retraction as well as fine detail required for an accurate impression. The high viscosity setting impression material 22 is a heavy body, higher viscosity matrix having a viscosity preferably greater than 400,000 cP, or backing material and that adheres to an impression tray and the low viscosity setting gingival retracting impression material, facilitating simultaneous removal of both materials 20 and 22. The high viscosity setting impression material 22 has sufficient body or viscosity to force and hold the low viscosity setting gingival retracting impression material 20 in and around the sulcus 12 or margin between the gingiva 14 and the prepared tooth 10. Both materials 20 and 22 have setting times that are synchronized so that both materials set at approximately the same time so that they adhere together. If desired, the low viscosity setting gingival retracting impression material 20 may be adjusted to have a slightly longer set time substantially equal to a time required to apply the high viscosity setting impression material 22 over the low viscosity setting gingival retracting impression material 20, so that both materials 20 and 22 set together either simultaneously or at approximately the same time.

An additional advantage of adjusting the set time of the low viscosity setting gingival retracting impression material 20 longer than the high viscosity setting impression material 22 is that as the high viscosity setting impression material 22 sets it gets stiffer or harder earlier than the low viscosity setting gingival retracting impression material 20 creating more of a backing for driving the low viscosity setting gingival retracting material 22 into the sulcus 12. This aids retraction and improves the resulting impression.

Figure 3:
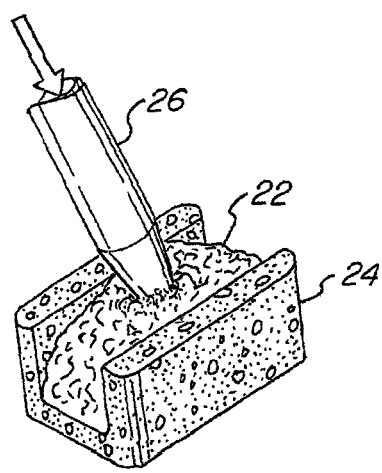
FIG. 3 schematically illustrates the placement of a high viscosity setting impression material in a dental tray.
Figure 4:
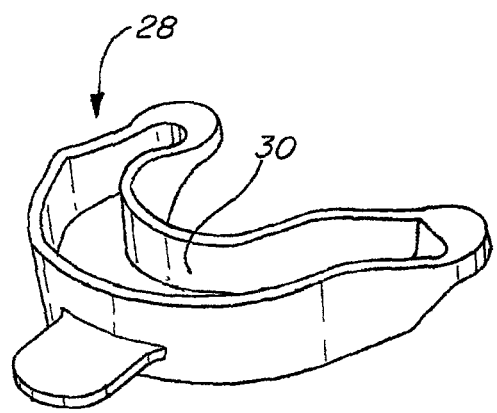
FIG. 4 illustrates a full dental tray.
Figure 5:
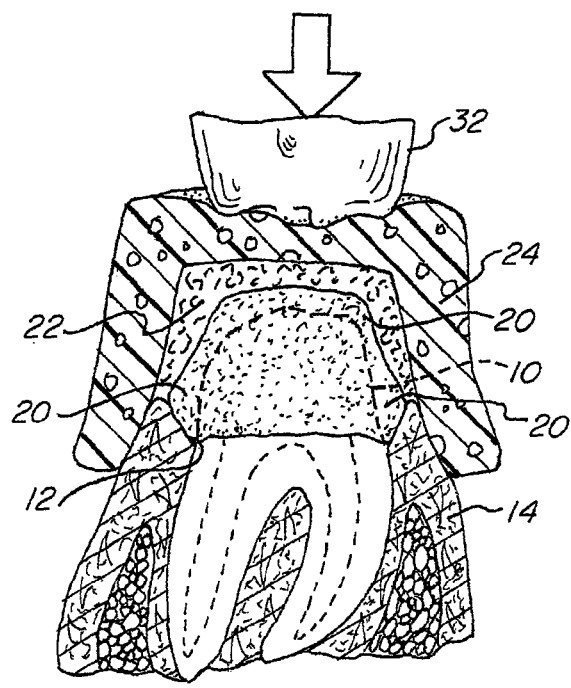
FIG. 5 schematically illustrates the placement of a dental tray over a prepared tooth.

The low viscosity setting gingival retraction impression material 20 is preferably applied around the sulcus 12 or margin between the prepared tooth 10 and the gingiva 14 with a syringe and syringe tip 16. The low viscosity setting gingival retraction impression material 20 is preferably placed over the entire exposed prepared tooth 10 surface. The high viscosity setting impression material 22 may be similarly applied with a syringe as illustrated in FIG. 2, but is preferably applied by first placing it in a dental impression tray, as illustrated in FIG. 3-5, and applied over the prepared tooth 10 and the low viscosity setting gingival retracting impression material 20 so as to form the impression. Therefore, after both materials 20 and 22 set and upon removal of the dental impression tray 24 or 30 both materials 20 and 22 are set and remain attached together as well as attached to the dental impression tray 24 or 28 so as to be removed in a single unit. This single unit or single unitary impression may then be used by a dental lab to prepare a crown, bridge, inlay, or overlay to fit over the prepared tooth 10.

FIGS. 3-5 illustrate a preferred technique or method for applying the high viscosity setting impression material. FIG. 3 illustrates the placement of the high viscosity setting impression material 22 into a quadrant or partial dental tray 24 or a full dental tray 28 having a groove or channel 30. The partial or full dental tray 24 and 28 maybe made of a porous flexible material or a non-porous rigid plastic material. The dental trays 24 or 28 need only be sufficiently rigid to prevent undue flexing so as to result in an accurate impression. The high viscosity setting impression material 22 may be placed in the dental trays 24 or 28 with a bulk syringe 26 having a nozzle. FIG. 4 illustrates a full dental tray which may also be used if a full dental impression is desired. A tray having different sizes for of any desired section or quadrant of the mouth may be used.

FIG. 5 schematically illustrates the low viscosity setting gingival retracting impression material 20, the high viscosity setting impression material 22, and a partial dental tray 24 applied to a prepared tooth 10. The low viscosity setting gingival retracting impression material 20 is placed into the sulcus 12 between the gingiva 14 and around and over the prepared tooth 10, preferably as illustrated in FIG. 1. The partial dental tray 24 is filled with the high viscosity setting impression material 22 and is positioned over the prepared tooth 10 so that the high viscosity setting impression material 22 is in contact with and covers the unset low viscosity setting gingival retracting impression material 20. Optionally, some of the high viscosity setting impression material 22 may be placed on the top of the prepared tooth 10 prior to placement of the filed cap or partial dental tray 24. Adjacent opposing tooth 32 may be used by the patient to apply pressure to the cap or partial dental tray 24.

The present invention is a unique dental impression system that makes taking a dental impression easier and more predictable. The low viscosity setting gingival retracting impression material stops fluid flow and controls bleeding and gently displaces the soft tissue or gingiva around the prepared tooth. The low viscosity setting gingival retracting impression material may contain more than 10%, and preferably 15% by weight of a retracting agent, such as aluminum sulfate. The retracting agent in combination with the low viscosity setting gingival retracting impression material and pressure applied by the high viscosity setting impression material retracts the gingiva widening the sulcus adjacent the prepared tooth creating a space permitting the low viscosity setting gingival retracting impression material to flow therein. This facilitates capturing all the margins resulting in a clear final impression.

The present invention is a gingiva retraction and impression system comprising use in combination of a low viscosity setting gingival retracting impression material and a high viscosity setting impression material. The system also comprises mixing nozzles and delivery tips used in a syringe, preferably having a mechanical advantage. The low viscosity setting gingival retracting impression material typically comprises two components that are mixed with a mixing nozzle and extruded through a delivery tip for placement around the prepared tooth. The high viscosity setting impression material also typically comprises two components that are mixed together with a mixing nozzle and extruded through a delivery tip. After mixing the two impression materials set. The system also comprises a dental tray in which the high viscosity setting impression material is placed before placement on the prepared tooth. The two impression materials work together in a single step to retract the gingiva and form an impression of the prepared tooth and margins. The impression is then used in making a crown, bridge, inlay, overlay or other dental work.

The single step gingival retraction and impression system of the present invention may be practiced according the following steps. Prepare the tooth for taking an impression and dry the area, place the low viscosity setting gingival retracting impression material into the gingival sulcus and around the tooth with a syringe, place the high viscosity setting impression material in a tray, placed the tray with the high viscosity setting impression material over the unset low viscosity setting gingival retracting impression material, apply pressure until the two impression materials are set, typically between 3 and 5 minutes, remove the tray together with the set two impression materials.

The present invention permits a clinician to take an accurate impression without the need for a prior retraction step. By combining the retraction necessary in a single step with taking an impression, the present invention saves time and cost, as well as makes dentistry easier.

What is claimed is:

1. A method for retracting gingiva and forming an impression of a prepared tooth comprising the steps of:
    placing a low viscosity setting gingival retracting impression material having a retracting agent and first viscosity around a prepared tooth;
    placing a high viscosity setting impression material having a second viscosity over the low viscosity setting gingival retracting impression material, wherein the second viscosity is higher than the first viscosity;
    selecting a first setting time for the low viscosity setting gingival retracting impression material and a second setting time for the high viscosity setting impression material wherein the first and second setting times are selected so that the low viscosity setting gingival retraction impression material and the high viscosity setting impression material set forming a single unitary mold of the prepared tooth;
    wherein the high viscosity setting impression material has a harder onset earlier than the low viscosity setting gingival retraction impression material; and
    removing the single unitary mold of the low viscosity setting gingival retracting impression material with the attached high viscosity setting impression material together,
    whereby gingiva surrounding the prepared tooth is retracted simultaneously with taking of an impression of the prepared tooth.

2. A method for retracting gingiva and forming an impression of a prepared tooth as in claim 1 wherein:
    the first viscosity ranges from 120,000 to 150,000 cP; and
    the second viscosity is greater than 400,000 cP.

3. A method for retracting gingiva and forming an impression of a prepared tooth as in claim 1 wherein:
    the retracting agent is selected from the group consisting of aluminum chloride, aluminum potassium sulfate, aluminum sulfate, alum, or ferric sulfate.

4. A method for retracting gingiva and forming an impression of a prepared tooth as in claim 1 wherein:
    the retracting agent comprises aluminum sulfate.

5. A method for retracting gingiva and forming an impression of a prepared tooth as in claim 1 further comprising the step of:
    placing the high viscosity setting impression material in a dental tray prior to said step of placing the high viscosity setting impression material having the second viscosity over the low viscosity setting gingival retracting impression material.

6. A method for retracting gingiva and forming an impression of a prepared tooth as in claim 5 wherein:
    the dental tray is a partial dental tray.

7. A method for retracting gingiva and forming an impression of a prepared tooth as in claim 5 further comprising the step of:

applying pressure to the dental tray towards the prepared tooth.

8. A method for retracting gingiva and forming an impression of a prepared tooth as in claim 1 wherein:
the high viscosity setting impression material is sufficient to force the low viscosity setting gingival retracting impression material into a sulcus around the prepared tooth.

9. A method for retracting gingiva and forming an impression of a prepared tooth as in claim 8 wherein:
the viscosity of the high viscosity setting impression material prior to setting is greater than 400,000 cP.

10. A method for retracting gingiva and forming an impression of a prepared tooth as in claim 1 wherein:
the high viscosity setting impression material also has a hardness when set greater than the low viscosity setting gingival retracting impression material.

11. A method for retracting gingiva and forming an impression of a prepared tooth as in claim 10 wherein:
the hardness of the high viscosity setting impression material when set is greater than eighty on a Shore hardness type A scale.

* * * * *